United States Patent [19]

Sanderson et al.

[11] Patent Number: 4,976,696
[45] Date of Patent: Dec. 11, 1990

[54] SYRINGE PUMP AND THE LIKE FOR DELIVERING MEDICATION

[75] Inventors: George Sanderson, Clark; Robert J. Strowe, Ramsey, both of N.J.

[73] Assignee: Becton, Dickinson and Company, Franklin Lakes, N.J.

[21] Appl. No.: 368,114

[22] Filed: Jun. 16, 1989

Related U.S. Application Data

[63] Continuation of Ser. No. 083,385, Aug. 10, 1987, abandoned.

[51] Int. Cl.$^5$ ............................................. A61M 37/00
[52] U.S. Cl. ...................................... 604/154; 604/65; 128/DIG. 12
[58] Field of Search ................. 604/154, 155, 31, 131, 604/67, 50; 128/DIG. 1, DIG. 12, DIG. 13; 200/523, 302.1, 302.2, 166, 245

[56] References Cited

U.S. PATENT DOCUMENTS

| 1,383,527 | 5/1921 | Cesaro ................................. 200/523 |
| 3,767,875 | 10/1973 | Schneikart et al. ............... 200/302.1 |
| 3,858,581 | 1/1975 | Kamen ................................. 604/155 |
| 4,024,864 | 5/1977 | Davies et al. ....................... 604/154 |
| 4,077,405 | 3/1978 | Haerten et al. ............... 128/DIG. 12 |
| 4,427,006 | 1/1984 | Nottke ............................. 200/302.2 |
| 4,465,474 | 8/1984 | Mardorf et al. ............... 128/DIG. 1 |
| 4,475,666 | 10/1984 | Bilbrey et al. ..................... 604/155 |
| 4,529,401 | 7/1985 | Leslie ............................... 604/155 |
| 4,544,369 | 10/1985 | Skakoon et al. ............. 128/DIG. 12 |
| 4,560,979 | 12/1985 | Rosskopf ........................... 604/154 |
| 4,581,509 | 4/1986 | Sanford et al. ................... 200/302.1 |
| 4,627,839 | 12/1986 | Young ................................. 604/154 |
| 4,684,767 | 8/1987 | Phalen ................................. 200/572 |
| 4,685,903 | 8/1987 | Cable et al. ....................... 604/154 |
| 4,695,271 | 9/1987 | Goethel ............................. 604/154 |
| 4,703,161 | 10/1987 | McLean ........................... 200/302.1 |
| 4,741,732 | 5/1988 | Crankshaw et al. ................ 604/155 |
| 4,791,258 | 12/1988 | Youtz et al. ....................... 200/302.1 |
| 4,794,215 | 12/1988 | Sawada et al. ................... 200/302.1 |
| 4,838,857 | 6/1989 | Strowe et al. ........................ 604/67 |

FOREIGN PATENT DOCUMENTS 2451197 11/1980 France ................................. 604/155

Primary Examiner—C. Fred Rosenbaum
Assistant Examiner—Kathleen A. Daley
Attorney, Agent, or Firm—Aaron Passman; Richard J. Rodrick

[57] ABSTRACT

A syringe pump comprises a housing and a retainer mounted thereon for receiving a syringe. The syringe to be received is of the type including a barrel for holding liquid medication and a plunger movably positioned in the barrel for expelling the liquid medication therefrom. A driver is movably mounted on the housing for engagement with the plunger and for pushing the plunger into the barrel to thereby force the liquid medication out of the barrel. A control mechanism within the housing regulates the movement of the driver against the plunger. This thereby regulates delivery of the liquid medication from the barrel. Depressible actuation buttons or switches are mounted on the housing for manual access by a user. These switches are associated with the control mechanism to permit the user to select one or more functions under which the control mechanism is to operate. The actuation switches include an electrically conductive material positioned to contact the control mechanism when depressed by the user. This depression causes an electrical energization or de-energization of the control mechanism for the operation of the selected function.

9 Claims, 9 Drawing Sheets

SYRINGE PUMP AND THE LIKE FOR DELIVERING MEDICATION

This application is a continuation of application Ser. No. 083,385, filed Aug. 10, 1987, now abandoned.

BACKGROUND OF THE INVENTION

1. Field of the Invention.

The present invention relates to a device to deliver or administer medication to a patient, and more particularly, concerns a syringe pump intended for the delivery or administration of such medications.

2. Background Description

Hospitals typically use intravenous (I.V.) administration sets to deliver liquid medication to patients. When the patient needs medication, such as an antibiotic, standard practice until recently has been to deliver such a drug by a "piggy-back" drip into the primary infusion line. Recently, however, the procedure for delivering antibiotics and other drugs to patients on I.V. therapy has been changing Mechanically driven syringes, oftentimes called or referred to as syringe pumps, are available to hospitals and other users for the administration of drugs and other liquid medications which the patient may require.

Indeed, a wide variety of syringe pumps and other liquid medication delivery devices are becoming available. With particular reference to a syringe pump, as that term is used herein, such pump employs a conventional or modified syringe which holds the liquid medication, the plunger of which is typically driven or pushed by a mechanized element for the automatic delivery of the liquid contents within the syringe. These syringe pumps are now available in battery-powered form, include microprocessor technology for programming rates or times of medication delivery, have digital displays for ease of viewing by the user or the patient, include alarm circuits in the event of duty cycle completion, failure, or line occlusion, and other features to facilitate the operation or performance of the syringe pump. As these syringe pumps become more sophisticated, the technological advances oftentimes have a tendency to increase the expense of making and using the device, increase the complexity of use, and increase the opportunities for breakdown and repair if one or more of the operational elements break down.

For example, many existing syringe pumps include an occlusion circuit for producing an alarm (visual and/or audible) when the syringe cycle has been completed, if the I.V. line or syringe is occluded or if there is a system failure. One common mechanism for activating the occlusion circuit has been the use of one or more switches which are tripped after the syringe plunger passes a certain point during its travel into the syringe barrel. In other instances, the syringe is mounted on a spring-loaded platform which is subject to a small linear movement after a certain force level has been reached. Thus, if the plunger being pushed into the syringe barrel either reaches the bottom of the syringe or cannot expel the liquid contents due to an occlusion in the line, the force against the plunger causes the entire spring-mounted syringe to move in linear fashion This movement, in turn, either trips a switch or may be sensed by position-sensitive sensors to send a signal to the occlusion circuit so that the automatic operation of the syringe pump may be terminated. Improvements in such an occlusion circuit are not only desirable, but are still being sought, in order to reduce the expense of the elements heretofore needed in such an occlusion circuit, as well as to eliminate the need for switches or sensing elements in order to achieve the desired results.

Some syringe pumps accept different size syringes for carrying different kinds or amounts of liquid medication. It is known to have an automatic measurement or sensing of the syringe size positioned in the syringe pump so that control of the rate and time of medication delivery may be automatically determined as a function of the size of the syringe placed in the syringe pump. Improvements in the sensing mechanism for accommodating and measuring different size syringes are desirable to provide a superior product.

Many available syringe pumps employ membrane switches on the front panel which the user depresses with a finger in order to activate a function of the syringe pump. These membrane switches, which include both on and off capabilities, are relatively expensive, and as the number of these switches increases with the sophistication of the functions, further it increases the expense of the entire device. Accordingly, improvements in the panel switches or buttons for access by the user are also desirable, and are being sought.

It is toward such improvements, as mentioned above, as well as other improvements to be pointed out below, that the present invention is directed.

SUMMARY OF THE INVENTION

The syringe pump of the present invention comprises a housing and a retainer mounted thereon for receiving a syringe. The syringe to be received is of the type including a barrel for holding liquid medication and a plunger movably positioned in the barrel for expelling liquid medication therefrom. A driver is movably mounted on the housing for engagement with the plunger and for pushing the plunger into the barrel to thereby force the liquid medication out of the barrel. Control means within the housing regulate the movement of the driver against the plunger to thereby regulate delivery of the liquid medication from the barrel. Depressible actuation means are mounted on the housing for manual access by a user. The actuation means are associated with the control means to permit the user to select one or more functions under which the control means operate. The actuation means include an electrically conductive material positioned to contact the control means when depressed by the user to electrically energize or de-energize the control means for the operation of the selected function.

In another embodiment of the present invention, the control means includes an electrically powered motor for moving the driver. An occlusion circuit is provided to stop the motor from moving the driver when delivery of liquid medication from the barrel has been completed or when an occlusion prevents liquid medication from being expelled from the barrel. This occlusion circuit is operative in response to a pre-set maximum current for operating the motor which, when reached, causes the motor to cease operation.

In a further embodiment of the present invention, the retainer includes first electrical contact means which are position-variable depending upon the size of the syringe received in the retainer. Second electrical contact means are within the housing and are positioned to be contacted by the first electrical contact means of the retainer for producing an electrical signal representative of the size of the syringe received in the retainer.

The electrical signal is receivable by the control means so that the movement of the driver may be related to the size of the syringe received in the retainer.

Another embodiment of the present invention includes a housing having an elongate bearing surface on an outside portion thereof. The driver is movably mounted on the housing and is in sliding contact with the bearing surface. Additionally, the driver is positioned for engagement with the plunger for pushing the plunger into the barrel for forcing the liquid medication out of the barrel.

In a further embodiment of the present invention, the housing includes a slot along which the driver assembly is movable. Protection means cover the slot and are cooperatively mounted in the housing to facilitate movement of the driver assembly with respect to the slot. The protection means provide a shield or curtain to prevent foreign materials from entering the interior of the syringe housing through the slot.

In accordance with the principles of the present invention, a number of improvements, such as those mentioned above, and other desirable advantages are provided by the syringe pump hereof. For example, the inclusion of an electrically conductive material as part of the actuation means permits the panel buttons or switches to appear and function in similar fashion to presently available membrane switches. However, the expense of the electrically conductive material, as part of the panel switches for access by the user, should be substantially lower than presently used flexible membrane switches. In addition, use of the electrically conductive material, such as graphite-impregnated silicone rubber, eliminates the need for wire connections between the front panel of the syringe pump device and the electrical circuit board included within the housing, as is presently required.

Another improvement and significant advantage of the present invention is in the novel occlusion circuit. As mentioned above, existing occlusion circuits rely on the mechanical tripping of a switching element or sophisticated sensor arrangements. In the present invention, these mechanical or mechanically-related switching elements the present invention operates in conjunction with the current limiting feature of the electrical motor used to drive the plunger into the syringe barrel. Accordingly, no switches or electrical elements need to be tripped in the present invention for the occlusion circuit to be activated.

A further advantage and improvement is provided by the present invention in the support arrangement for the sliding movement of the driver which pushes the plunger into the syringe barrel. In known and existing syringe pumps, the driver is typically coupled by a half-nut arrangement to a lead screw which is rotated by the electrical motor. Guide rails are normally provided as bearing surfaces to support the linear movement of the driver as it is driven by the lead screw. Two of these guide rails are normally arranged in parallel tracks in the same direction as the lead screw. In the present invention, however, there are no guide rails. Instead of guide rails, a bearing surface is preferably provided on the outside surface of the housing, in the form of raised surfaces. The driver is coupled to a lead screw within the housing, but slides along the raised bearing surfaces of the housing itself for support while operation is underway. Elimination of the guide rail arrangement not only saves expense, but also reduces the weight of the device since the known guide rails are typically made out of metal such as stainless steel.

Still further, another advantage of the present invention is found in the arrangement which permits syringes of different sizes to be retained on the syringe pump. In addition to accepting syringes of different sizes, it is a feature of the present invention that the size of the syringe be automatically measured or sensed so that size-related information may be directed to the microprocessor which controls the operations and functions of this syringe pump. In presently known and available syringe pumps, such a feature for sensing different size syringes includes the use of electrical contacts within the syringe clamp mounted on the outside of the housing. Wire connections had to be made between the electrical contacts on the syringe clamp outside of the housing and the electrical circuit board within the housing. In the present invention, however, no such wire connections are required because electrical contacts are provided directly between the syringe clamp or retainer and the electrical circuit board inside the syringe pump housing. This arrangement minimizes manufacturing steps as well as simplifying the design and operation of the syringe pump.

Other advantages, improvements, and features of the present invention will become more apparent upon reading the detailed description below.

DETAILED DESCRIPTION

Figure 1:
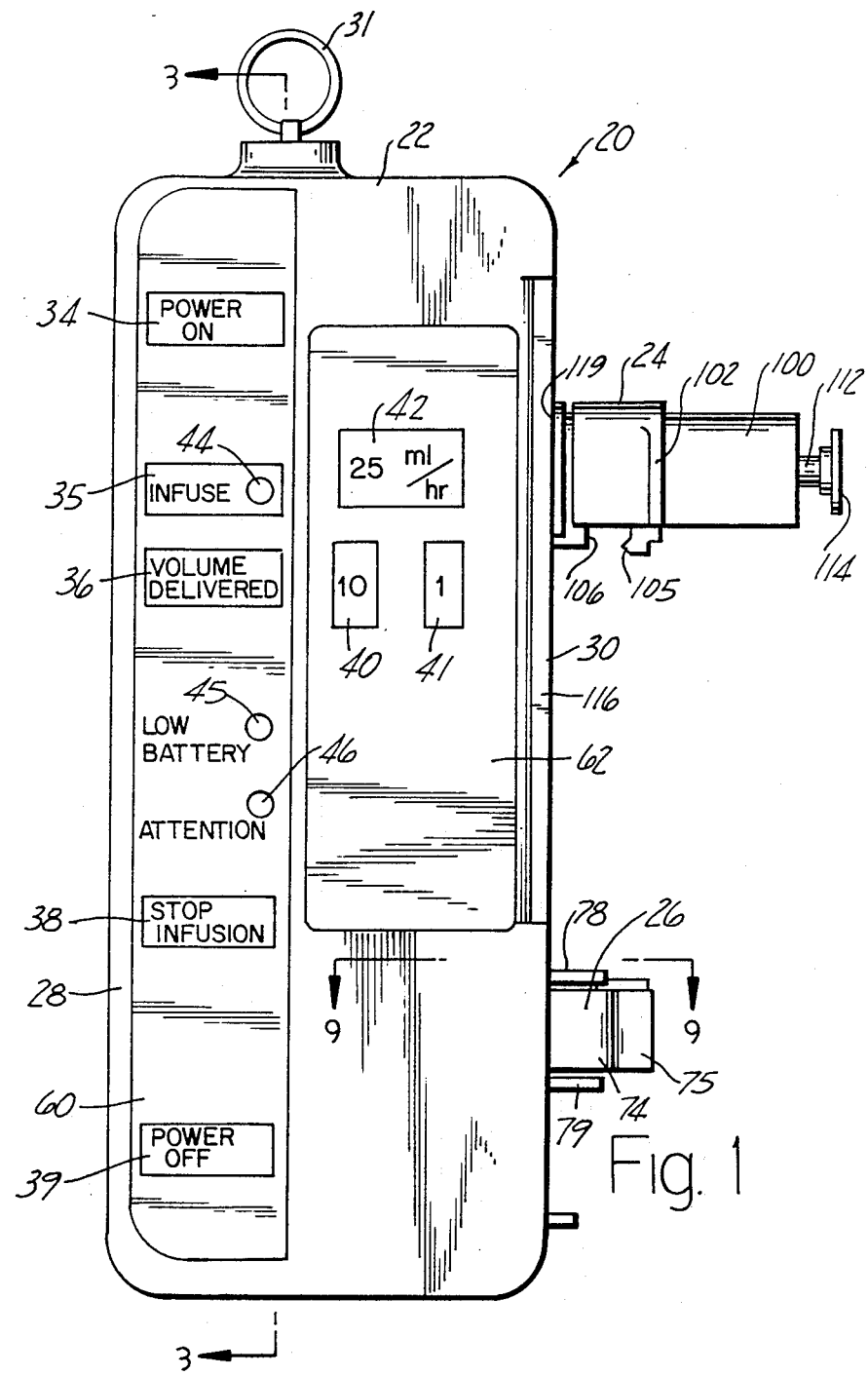
FIG. 1 is a plan view of the preferred embodiment of the syringe pump of the present invention illustrating the front face thereof as it appears to a user.

While this invention is satisfied by embodiments in many different forms, there is shown in the drawings and will herein be described in detail a preferred embodiment of the invention; with the understanding that the present disclosure is to be considered as exemplary of the principles of the invention and is not intended to limit the invention to the embodiment illustrated. The scope of the invention will be measured by the appended claims and their equivalents.

Figure 2:
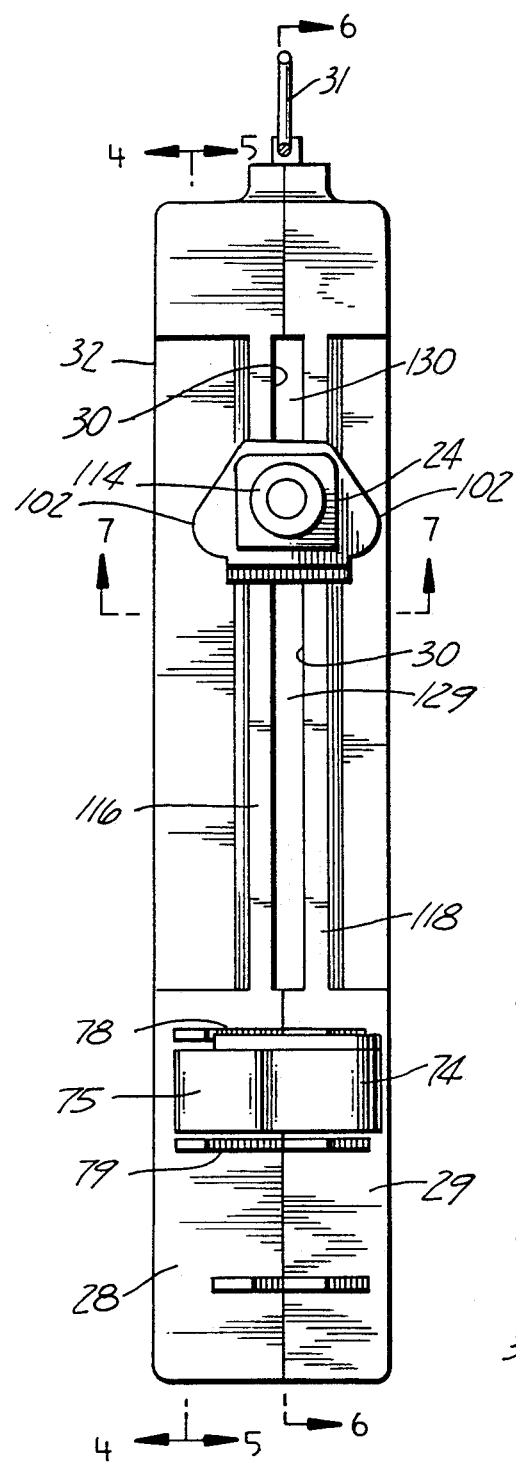
FIG. 2 is a side view of the syringe pump of FIG. 1 looking toward the side having the driver for moving the plunger and the retainer for mounting the syringe barrel.

Adverting now to the drawings, and FIGS. 1 and 2 in particular, there is shown a syringe pump 20 in a preferred configuration for purposes of the present invention. In general, syringe pump 20 is comprised of a housing 22, a driver mechanism 24 and a syringe retainer 26. In the preferred configuration, housing 22 is a compact, light-weight housing which is assembled in two parts, consisting of an upper (front) cover 28 and a lower (back) cover 29. Each of covers 28 and 29 is preferably formed in tray-like fashion so as to be able to include the interior components of the syringe pump, as well as for ease of assembly with a few screws or the like. When assembled, it is preferred that covers 28 and 29 form housing 22 which is completely enclosed except for an elongate slot 30 on one side of the housing. This slot, as will be described more fully hereinafter, permits driver 24 to move outside of the housing while being driven by a drive mechanism within the housing. A ring 31 is connected to the housing to provide a hook or the like for hanging the syringe pump on a stand at the location where the patient is to receive the medication from the syringe pump.

Upper cover 28 includes a front face 32 with a number of controls and displays. It is understood that many different controls or displays may be provided in a syringe pump depending upon a variety of factors and intended functions thereof. For purposes of the present invention, and while suggesting no limitations, upper face 32 includes five control mechanisms or buttons, namely, "POWER ON" 34, "INFUSE" 35, "VOLUME DELIVERED" 36, "STOP INFUSION" 38, and "POWER OFF" 39. Two other buttons or controls are provided, one such button 40 permitting the user to increment the rate of delivery of medication by "10's" and the other control or button 41 permitting the user to increment the rate of medication delivery by "1's." When buttons 40 and 41 are depressed by the user, a display 42 digitally indicates the numbers that have been incrementally selected by the user. Each time buttons 40 and 41 are pushed, the digit in the "1's" or "10's" columns are incremented by one until the number selected by the user is displayed. In the embodiment being described, display 42 usually shows the rate of delivery of medication, in milliliters per hour, to be selected by the user.

In addition to display 42, INFUSE button 35 has a light display 44 associated therewith so that the light is turned on when the INFUSE button has been pushed to inform the user that infusion is taking place. Another panel light 45 is provided to indicate when the batteries are low. A third panel light 46 is provided as an ATTENTION indicator serving as a visual alarm to inform the user that the syringe is empty or that an occlusion has occurred and infusion has been terminated.

Figure 3:
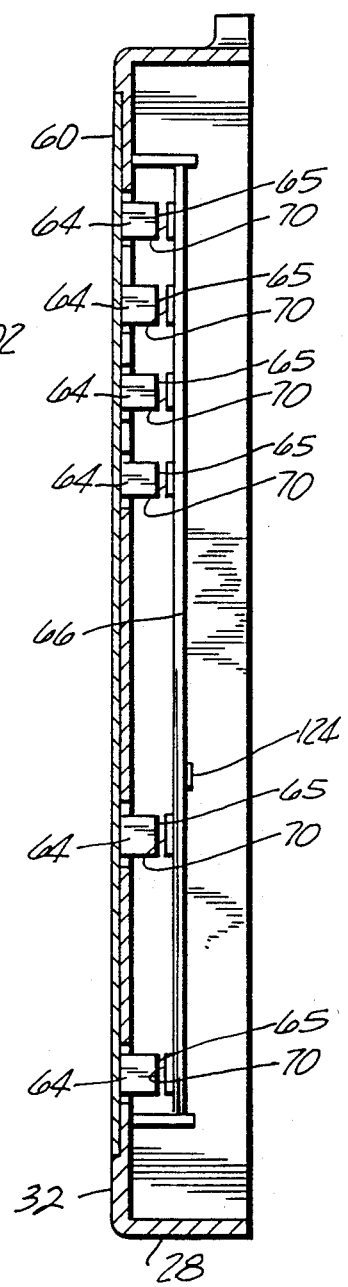
FIG. 3 is a cross-sectional view of the front cover of the syringe pump housing taken along line 3—3 of FIG. 1.
Figure 4:
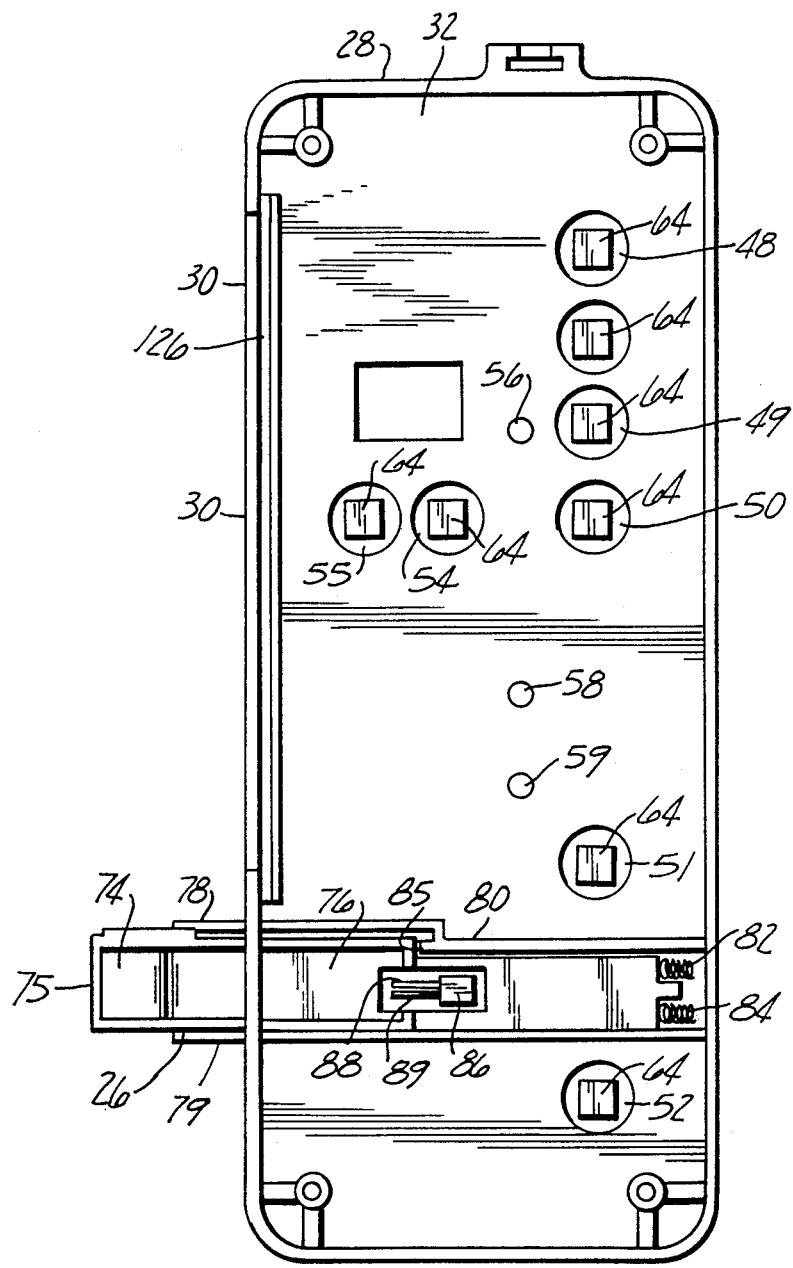
FIG. 4 is a cross-sectional view of the interior face of the front cover of the syringe pump taken along line 4—4 of FIG. 2.
Figure 5:
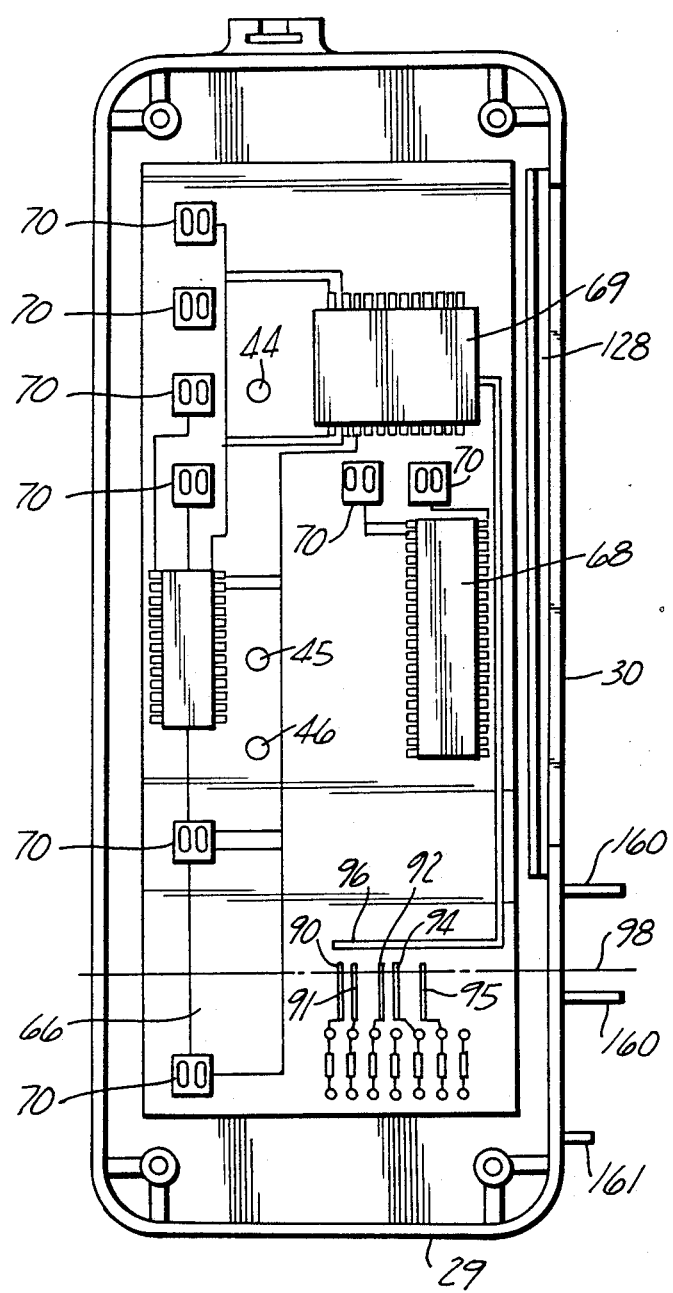
FIG. 5 is a cross-sectional view of the interior components of the syringe pump, particularly illustrating one surface of the printed circuit board, as these components appear just inside the front face of the syringe pump of the present invention, taken along line 5—5 of FIG. 2.

The mechanism of actuation of the various controls on the front face of the upper cover is more clearly seen by referring to FIGS. 3–5, taken in conjunction with FIG. 1. Looking first at FIG. 4, upper cover 28 is illustrated as it appears looking from the inside. A number of holes are provided through front face 32 of cover 28 and these holes, designated by numerals 48, 49, 50, 51, 52, 54 and 55 correspond with buttons 34, 35, 36, 38, 39, 40 and 41, respectively. Holes 56, 58 and 59 correspond with lights 44, 45 and 46, respectively. The holes associated with the buttons are covered by a thin, flexible and depressible membrane 60, preferably in one piece extending over the entire front face of the upper cover, on the left-hand side thereof as illustrated in FIG. 1. A similar thin, flexible, depressible membrane 62 covers holes 54 and 55 associated with the buttons for regulating display 42, and this membrane covers a substantial portion of the right-hand side of the upper cover as seen in FIG. 1. Of course, it is understood that the depressible membranes may be separate for each button or control to be depressed or may be a singular membrane covering the entire surface of the front cover where depressible buttons are included. Affixed to the bottom side of membranes 60 and 62, and extending through each hole associated with a button or control, is an electrically conductive piece of material 64. Material 64 is preferably in the form of a block so that it has a substantially flat end surface 65 for electrical contact purposes. Material 64 may be any electrically conductive material, such as metal, including copper, aluminum and the like, but is preferably a compressible material with spring-like qualities so as to be compatible with being depressed in button-like fashion. For example, this material may be styrofoam or other lightweight and inexpensive material, with an electrically conductive end 65 for electrical contact purposes. On the other hand, an inexpensive and lightweight material such as graphite-impregnated silicone rubber is quite suitable for the present invention insofar as this material is electrically conductive and is compressible as well.

In FIGS. 3 and 5, it can be seen that there is a printed circuit board 66 mounted within upper cover 28 so that it is spaced inwardly from front face 32. This printed circuit board includes the electrical circuitry for operation of the syringe pump and includes a variety of electrical components including one or more microprocessors 68 and/or associated integrated circuit chips, a digital readout 69 for display 42, panel lights 44, 45 and 46, and other circuits and components well within the purview of the ordinary artisan for completing the electrical functions as explained herein. Part of the circuitry on printed circuit board 66 includes switching circuits for controls 34, 35, 36, 38 and 39, and stepper circuits for controls 40 and 41. These circuits are energized by momentarily closing the circuits associated therewith, and then are de-energized by momentarily closing the circuits with the same switching mechanism.

For each control button on the front panel of the housing, the printed circuit board includes an electrically conductive pad 70, in this instance, composed of two electrical elements of the circuit associated therewith. These electrically conductive pads are positioned on the printed circuit board so that they are slightly spaced and directly opposed from face 65 of block of material 64. This close spacing between face 65 and electrical pad 70 is more clearly illustrated in FIG. 3. For example, this spacing may be about 0.020 inches (0.51 millimeters). When the user pushes the area of membrane 60 or 62 with one of the control buttons, the membrane deforms under the force of depression, causing block 64 to move toward electrical pad 70 so that face 65 of each block 64 makes contact with pad 70. This electrical contact causes a momentary bridging between the two electrical elements on the electrical pad in question, in turn energizing the electrical circuit affected by the control button being depressed, so that the desired operation of the selected function may occur. When the depression force is released by the user, contact is broken between face 65 of block 64 and electrical pad 70, and the subsequent depression of the same control button against the related pad causes a momentary electrical contact between face 65 and pad 70, this time de-energizing the affected electrical circuit. With respect to control buttons 40 and 41, successive deprescriptions thereof cause the display to increment to the next higher number in the column associated with the button being pushed. It is observed that the electrical actuation mechanism, described above, causes the electrical circuits and functions to be energized and de-energized without the need for wire connections between the depressible control button and the printed circuit board on which the circuits are maintained.

Reference is now made to FIGS. 1, 2, 4 and 5 in which the details of syringe retainer 26 are more clearly illustrated. Retainer 26 preferably includes a slidable clamp 74, which has a portion extending outside of the housing in the form of a downwardly depending arm 75 and a portion extending inside the housing in the form of a relatively flat strip 76. A pair of clamp guides 78 and 79, affixed to upper cover 28, hold clamp 74 in position and serve to guide the movement of the clamp for holding the syringe barrel in position with respect to the housing. Inside upper cover 28 are a pair of tracks 80 and 81 between which flat strip portion 76 of the clamp is positioned. Thus, guide clamps 78 and 79 and tracks 80 and 81 not only maintain the clamp in position with respect to the upper cover, but facilitate the sliding movement of the clamp in and out of the upper cover in a lateral direction as viewed in FIG. 4. Connected to one of the walls of upper cover 28 is a pair of springs 82 and 84, which, in turn, are connected to the interior end of flat strip portion 76 of clamp 74. These springs are selected so that an inward bias is maintained on clamp 74 so that when the syringe barrel is held in place against the housing by virtue of depending arm 75, an inward force is applied to the syringe barrel to keep the syringe barrel securely in place. It is appreciated that springs 82 and 84 are stretchable in order to accommodate larger size syringe barrels by permitting the clamp to slide outwardly a further distance from the housing surface, as will be described in greater detail hereinafter. Track 80 includes a shoulder 85 which serves as a stop device to limit travel of clamp portion 76 inwardly toward the springs, thereby keeping a constant bias on the clamp.

Mounted on the bottom of clamp portion 76 is an electrical contact member including two electrical tabs 88 and 89. When housing 22 is assembled, and upper cover 28 is positioned over lower cover 29, electrical tabs 88 and 89 are positioned to be able to contact printed circuit board 66. Specifically, and with particular reference to FIG. 5, printed circuit board 66, in the area juxtaposed with strip portion 76 of the clamp, includes a plurality of electrical contact strips, in this instance five in number designated by numerals 90, 91, 92, 94 and 95. These electrical strips are arranged laterally across the face of the printed circuit board in spaced fashion. Another electrical strip 96 is spaced slightly adjacent to the aforementioned electrical strips, and this strip 96 extends laterally so that it traverses the entire width of the separated, individual strips located slightly therebelow. All of these electrical strips are connected to the electrical circuitry on the printed circuit board.

Strip portion 76 of clamp 74 is arranged so that it is slidable inwardly and outwardly along axis 98. Irrespective of the position of clamp 74, electrical tab 88 is intended to be in constant contact with electrical strip 96; depending upon the position of clamp 74, electrical tab 89 contacts one of electrical strips 90, 91, 92, 94 or 95. When one of these latter mentioned strips is contacted, such strip along with electrical strip 96 serves to energize a circuit sending a signal to the microprocessor representative of the size of the syringe barrel mounted against the housing.

In particular, strips 90, 91, 92, 94 and 95 are positioned and spaced on the printed circuit board, and in conjunction with the design of clamp 74 including the location of electrical tabs 88 and 89, so that certain size syringe barrels may be sensed. For example, and without suggesting any limitations, if a 5 cc syringe barrel is mounted against the housing by the retainer clamp, electrical tab 89 is in electrical contact with electrical strip 90 (electrical tab 88 also being in contact with electrical strip 96). A closed circuit is thus established between electrical strips 90 and 96 sending a signal to the microprocessor indicative of the presence of a 5 cc syringe being used. The microprocessor preferably includes memory storage capability for identifying this electrical signal received from the aforementioned electrical contacts so that the functions of the syringe pump which occur will relate to the performance of a 5 cc syringe. In similar fashion, contact between tab 89 and electrical strip 91 may represent a 10 cc syringe; contact between electrical tab 89 and electrical strip 92 may represent a 20 cc syringe; electrical contact between tab 89 and electrical strip 94 may represent a 30 cc syringe; and electrical contact between tab 89 and electrical strip 95 may represent a 60 cc syringe. The microprocessor and the electrical circuitry is preferably pre-programmed to identify the different signals caused by the different electrical contacts so that operation of the syringe pump can be performed automatically without the necessity of the user having to inform the syringe pump which size syringe is being utilized. It is appreciated that the linear traverse of the retainer clamp for making contact with the electrical strips on the printed circuit board eliminates the need for any wiring between the clamp and the printed circuit board for establishing the various circuits for energizing or de-energizing the functions to be performed by the present syringe pump.

Figure 6:
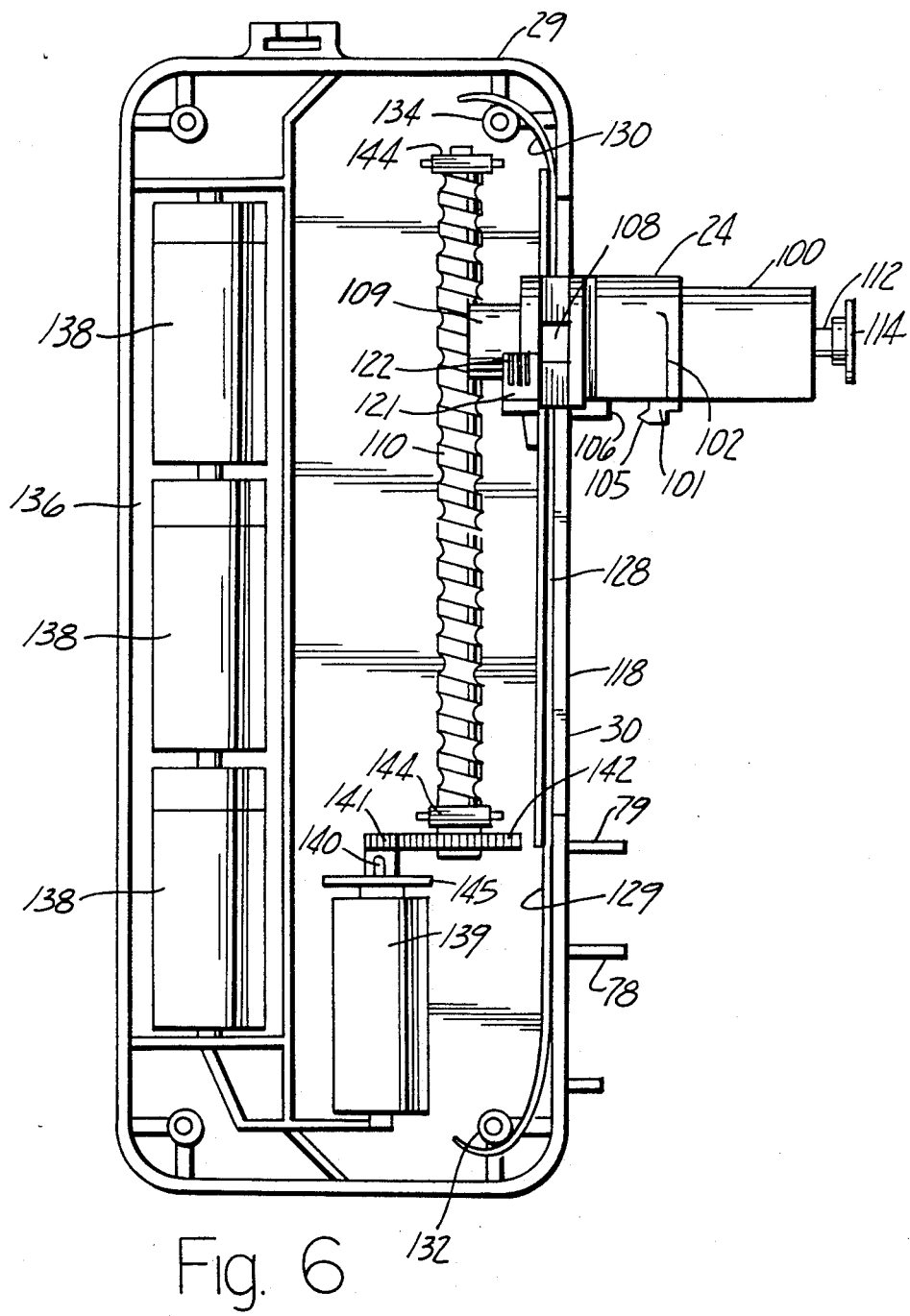
FIG. 6 is a cross-sectional view of the interior components of the syringe pump positioned below the printed circuit board as such components are positioned inside the back cover of the syringe pump housing, taken along line 6—6 of FIG. 2.
Figure 7:
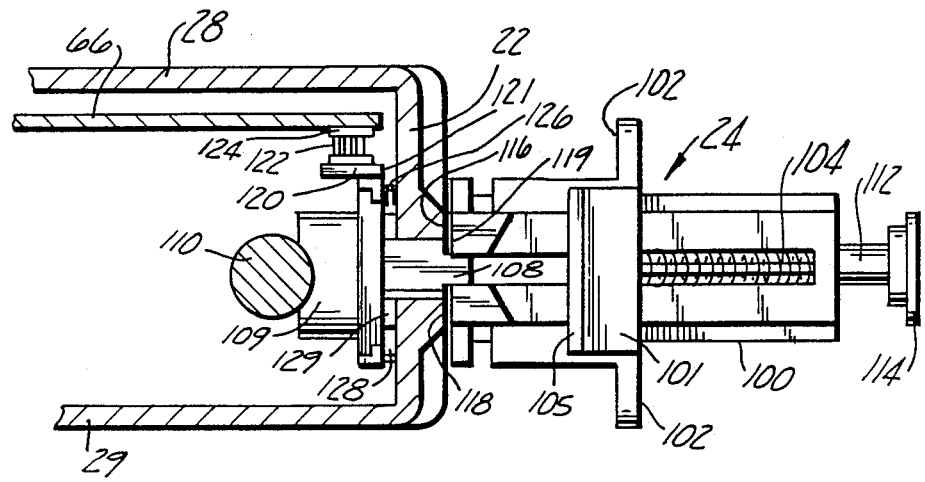
FIG. 7 is an enlarged cross-sectional view of a driver mechanism of the present invention taken along line 779 of FIG. 2.

FIGS. 6 and 7, along with FIGS. 1 and 2, more clearly illustrate the details of driver 24 as it is mounted on housing 22. Driver 24 is an assembly including a body member 100 to which is attached a slidable latch member 101. Latch member 101 preferably has outwardly protruding finger flanges 102 for easy grasping by the user. A spring, such as coil spring 104, is preferably included within body member 100 so that a force is urged against latch member 101 keeping it biased in an inward direction toward the housing. Latch member 101 may be moved outwardly by grasping the finger flanges and applying sufficient outward force to overcome the biasing force of spring 104. In conjunction with the slidable movement of latch member 101, there is provided a catch or hook 105 which facilitates the holding of the plunger of the syringe in position against driver assembly 24. An abutment 106 is provided on body member 100 serving as a fixed element also for holding the plunger of the syringe in position against the driver assembly. Positioning of the syringe, with its extended plunger, will be described more completely hereinafter.

Body member 100 includes a shank 108 extending through slot 30 of housing 22. On the interior side and connected to shank 108 is a half-nut mechanism 109 positioned to engage the threads of a lead screw 110. When half-nut 109 is engaged to lead screw 110, rotation of the lead screw imparts linear movement to driver 24 by virtue of the half-nut threaded engagement. This type of driving arrangement is well-known in the art of syringe pumps and no further details need be provided for a complete appreciation of the working of such elements.

In order to provide disengagement between half-nut 109 and lead screw 110, a disengagement rod 112 extends through body member 100 so that its interior end is associated with half-nut 109. Although not shown in FIG. 7, rod 112 is spring-loaded so that its exterior end extends a short distance beyond the end of body member 100. A thumb button 114 is preferably included at the exterior end of rod 112 so that the thumb or finger of the user may depress rod 112 inwardly. Depression of rod 112 inwardly, with sufficient force to overcome the spring-loading effect thereof, causes half-nut 109 to become disengaged from lead screw 110. When disengagement of these parts occurs, driver mechanism 24 is freely slidable along slot 30 so that it may be moved to any position along the slot, such as an initial position for latching onto the plunger rod of the syringe when the syringe is being loaded It is preferred that the depression of rod 112 for disengagement of the half-nut from the lead screw be independent of the slidable movement of latch member 101 for making the connection to the plunger rod of the syringe.

Currently available syringe pumps rely on guide rails or the like for providing bearing support to the driver mechanism as it moves in linear fashion as a result of rotation of the lead screw. Instead of guide rails, the present invention relies upon the unique construction of housing 22 to provide adequate bearing surfaces for supporting the driver mechanism during its linear movement along the housing. Specifically, it can be seen particularly in FIG. 7 that upper housing 28 and lower housing 29 are formed so that slot 30 lies between the two housing portions when joined together It can be seen that upper housing portion 28 includes a raised bearing surface 116 and lower housing portion 29 includes a raised bearing surface 118, with each such bearing surface extending along the elongate dimension of slot 30 and running substantially parallel thereto. Bearing surfaces 116 and 118 provide sliding support for driver mechanism 24 at portion 119 of body member 100. This support is provided at this interface when the driver mechanism is engaged to the lead screw and also when it is disengaged therefrom.

In FIGS. 6 and 7, it can be seen that a small platform 120 is mounted on the driver mechanism near the half-nut component, on the interior side of housing 22. Platform 120 is preferably an electrical insulator, such as rigid plastic or the like. Mounted on platform 120 is an electrical contact member 121 including one or more electrical contacts 122. These electrical contacts 122 are arranged so that they are in contact with one side of printed circuit board 66. One or more electrical pads 124 are provided on the surface of printed circuit board 66 so that electrical contacts 122 may come in contact therewith. Electrical pads 124 are preferably positioned on the printed circuit board at a position near the end of elongate slot 30 where the driver mechanism will finish its movement when the plunger rod has been moved all or almost all of the way into the syringe for emptying the contents thereof. A relative position of electrical pads 124 with respect to slot 30 may be seen by briefly referring to FIG. 3. This contact between electrical contacts 122 and electrical pads 124 is part of an occlusion circuit to be described more fully hereinbelow.

Figure 8:
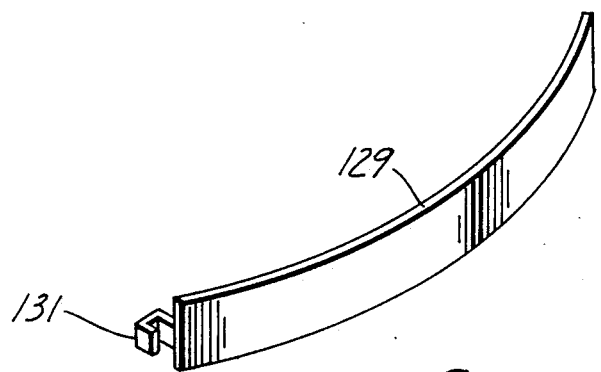
FIG. 8 is an enlarged perspective view of the curtain for protectively covering the elongate slot through which the driver mechanism is controlled.

Included in the syringe pump of the present invention is a protective feature for covering the opening made by the elongate slot along the side of the housing. In presently known and available syringe pumps, such a slot is frequently left uncovered, in which case, fluids may spill therethrough into the interior of the housing; further, small objects such as portions of clamps, clips or the like, may slip through the slot and enter the housing, potentially causing some damage or malfunction. In order to overcome this deficiency in the known syringe pumps, the present invention provides a protective covering with respect to the slot. In particular, and as seen in FIGS. 4–7, upper housing cover 28 includes an elongate groove 126 formed just inside and extending substantially parallel to slot 30. In similar fashion, lower housing cover 29 includes an elongate groove 128 also formed just inside of and extending substantially parallel to slot 30. When upper cover 28 and lower cover 29 are assembled, grooves 126 and 128 face each other and form a channel. Positioned in this channel, and preferably connected to drive mechanism 24, are two flexible bands 129 and 130. Bands 129 and 130 are preferably similar in construction, and are substantially flat, elongate and flexible in nature. As seen in FIG. 8, one end of band 129 includes a hook 131 which fits into a depression or hole (not shown) on driver mechanism 24. Band 129 fits in grooves 126 and 128 and extends from driver mechanism 24 over slot 30 and bends around a drum-like element 132 (primarily used for a screw attachment). Similarly, band 130 sits in grooves 126 and 128 and extends from its attachment to the driver assembly over the interior portion of slot 30 and bends around another drum-like element 134 at the other corner of the housing.

The flexible nature of these bands allows them to remain in position covering the interior side of slot 30 when driver mechanism 24 moves along the slot. Bands 129 and 130 move with the driver mechanism thereby providing constant protection of the slot so that foreign materials may be prevented from entering the housing through the slot.

Figure 9:
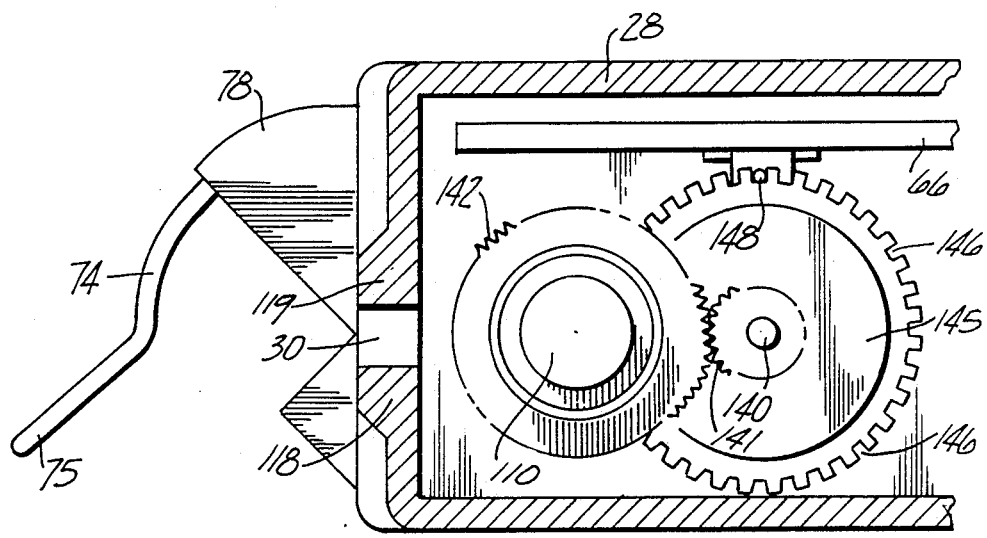
FIG. 9 is an enlarged cross-sectional view illustrating the motor mechanisms and lead screw arrangement inside the syringe housing taken along line 9—9 of FIG. 1.

Turning now to FIG. 6, it can be seen that lower housing portion 29 includes a compartment 136 which holds one or more batteries 138 to provide electrical power for operating the motor and electrical circuitry of the present syringe pump. These batteries provide direct current (DC) to a motor which is preferably a DC motor 139, for driving and rotating lead screw 110. Motor 139 includes a shaft 140, which is also illustrated in FIG. 9, taken in conjunction with FIG. 6. Attached to shaft 140 is a small gear 141 which rotates when shaft 140 rotates when the motor is operating. Another gear 142, in this case a larger gear, is connected to lead screw 110 and is in meshing engagement with smaller gear 140. Accordingly, operation of motor 139 causes the rotation of lead screw 110 by virtue of the rotating shaft of the motor and the associated gears. Lead screw 110 is maintained in position within lower housing portion 29 preferably by means of journal bearings 144 positioned at or near the respective ends of lead screw 110.

Also connected to drive shaft 140 of DC motor 139 is a wheel 145 which serves as an encoder associated with the timing and the control circuitry governing the operation of the present syringe pump. Encoder 145, being connected to drive shaft 140 of the motor, therefore rotates when shaft 140 rotates. It can be seen, particularly when viewing FIG. 9, that encoder 45 is divided into a plurality of equally spaced gaps or segments 146 arranged around the periphery thereof. These gaps or segments pass in front of a light such as a light emitting diode (LED) 148 connected to printed circuit boards 66, so that the number of segments may be counted for operation of the control circuit as part of the electrical circuitry hereof.

During operation of DC motor 139, for each passage of a segment 146 of the encoder past LED 148 lead screw 110 rotates to cause the drive mechanism 24 to move a fixed linear distance. In turn, this movement causes the movement of the syringe plunger into the syringe barrel, as will be pointed out below. As the syringe plunger is moved into the syringe barrel by a known, fixed distance, such linear movement of the plunger may be translated into a known volume. Thus, it is possible to calculate the volume of liquid delivery from the syringe in milliliters per segment or increment, for each passage of a segment of the encoder. For different size syringes, this volume per increment will vary. This information o volume per increment for different size syringes, preferably of the conventional size syringes used in hospital procedures, is stored in the memory function of microprocessor 68 included in the electrical circuitry of the control functions of the present syringe pump. In connection with the microprocessor and the selectable functions of the present invention, if the desired delivery rate, in milliliters per hour, is programmed or selected for operation by a user of the syringe pump, the time between increments may be determined by dividing the delivery rate (milliliters per hour) by the volume per increment (milliliters per increment). This calculation is preferred automatically by the electrical circuitry and is also storable in the memory function of the microprocessor hereof to provide the time between increments. Total volume of liquid medication to be delivered from the syringe may be established or calculated by multiplying the total number of increments of the motor by the volume per increment of the particular syringe in use. As pointed out above, each increment of the motor is determined by the passage of segment 146 of encoder 145 in conjunction with LED 148. The electrical circuitry of the present invention includes a timing circuit which is designed to account for the time intervals to be calculated as mentioned above, associated with the desired delivery rates for different size syringes.

Figure 10:
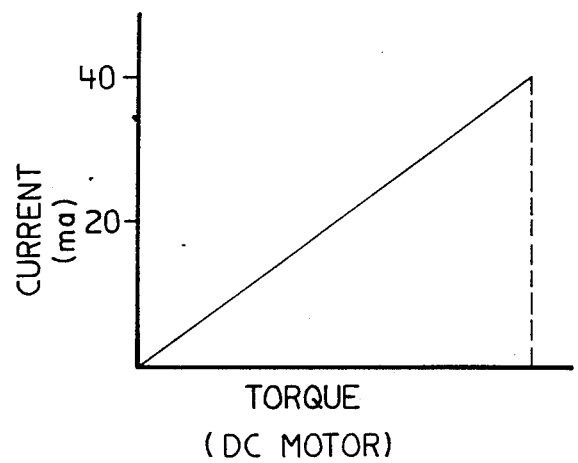
FIG. 10 is a graphical representation of the performance of the DC motor in terms of current versus torque according to the principles of the present invention.

An occlusion detection circuit is included in the electrical circuitry and relies on the physical property of DC motors and the aforementioned timing circuit to carry out its intended functions. The occlusion circuit is intended to inform the user when the medication delivery from the syringes barrel has been completed (sometimes referred to as end of cycle) and also to inform the suer when delivery of medication from the syringe is prevented or substantially altered because of an occlusion or the like in the fluid delivery line. In connection with the particular properties of DC motors, appropriate circuitry is provided to the instant DC motor so that it is current limited. As a result, the amount of torque the motor can apply for rotating the lead screw, for ultimately pushing the plunger into the syringe barrel, is also limited, in a relationship such as illustrated in FIG. 10. For example, under normal operation of the instant DC motor, the current may typically run about 20 milliamps under normal torque conditions. In the event that the torque increases to about 40 milliamps, because of the increased pressure in the syringe barrel due to occlusion or end of cycle, the current increases in linear fashion to maintain operation of the motor. The current limitation of the present invention, however, causes the motor to stop operation when the current reaches the threshold level set by the current limiting circuitry.

At the beginning of the initial timing increment of operation, DC motor 139 is turned on and a control circuit is set in accordance with the electrical circuitry thereof. Should there be a line occlusion or end of cycle, the force to move the plunger rod into the syringe barrel increases. This, in turn, causes the torque of the DC motor to increase. Accordingly, the current increases, and at the current limiting threshold, the motor stalls and stops operation. As a result, the DC motor does not complete its movement to the next segment 146 of encoder 145. In normal operation, when motor 139 reaches next encoder segment 146, it activates the electrical circuitry to turn the motor off and to reset the control circuitry. However, in the event of an occlusion which causes DC motor 139 to cease operation, the control circuitry is not reset. On the other hand, the control circuit receives the next time increment from the timing circuit and recognizes that the last increment has not be completed, and therefore activates the alarm circuitry. This alarm circuitry, as pointed out above, lights attention signal 46 on the front face of housing 22, and may also activate an audible alarm If an occlusion occurs because of fluid delivery line blockage or the like, the audible alarm is programmed to provide a rapid beeping sound or rapid flashing of light 46 on the face of the panel. If, however, the occlusion circuit is activated because of end of cycle and medication delivery from the syringe barrel has been completed, a different alarm is preferably activated. In the case of end of cycle, driver mechanism 24 has moved in linear fashion along slot 30 so that the syringe plunger is almost completely pushed within the syringe barrel. At this location, electrical contacts 122 on driver mechanism 24 come in contact with electrical pad 124 on printed circuit board 66. This contact serves as a switch or the like causing the occlusion detection circuit to issue an alarm different from the alarm mentioned above with respect to blockage in the delivery line. The end of cycle alarm may be a slow beeping signal or slow flashing of light 46 on the front panel of the housing.

Figure 11:
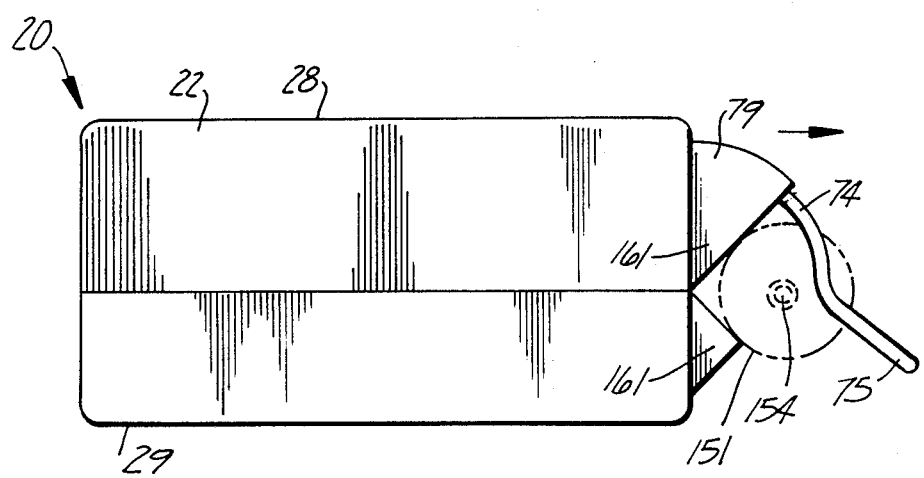
FIG. 11 is an end view of the syringe pump of FIG. 1 illustrating the mounting of a syringe by virtue of the retainer clamp, further illustrating the syringe barrel positioned against the housing and the clamping position of the retainer clamp shown in phantom.
Figure 12:
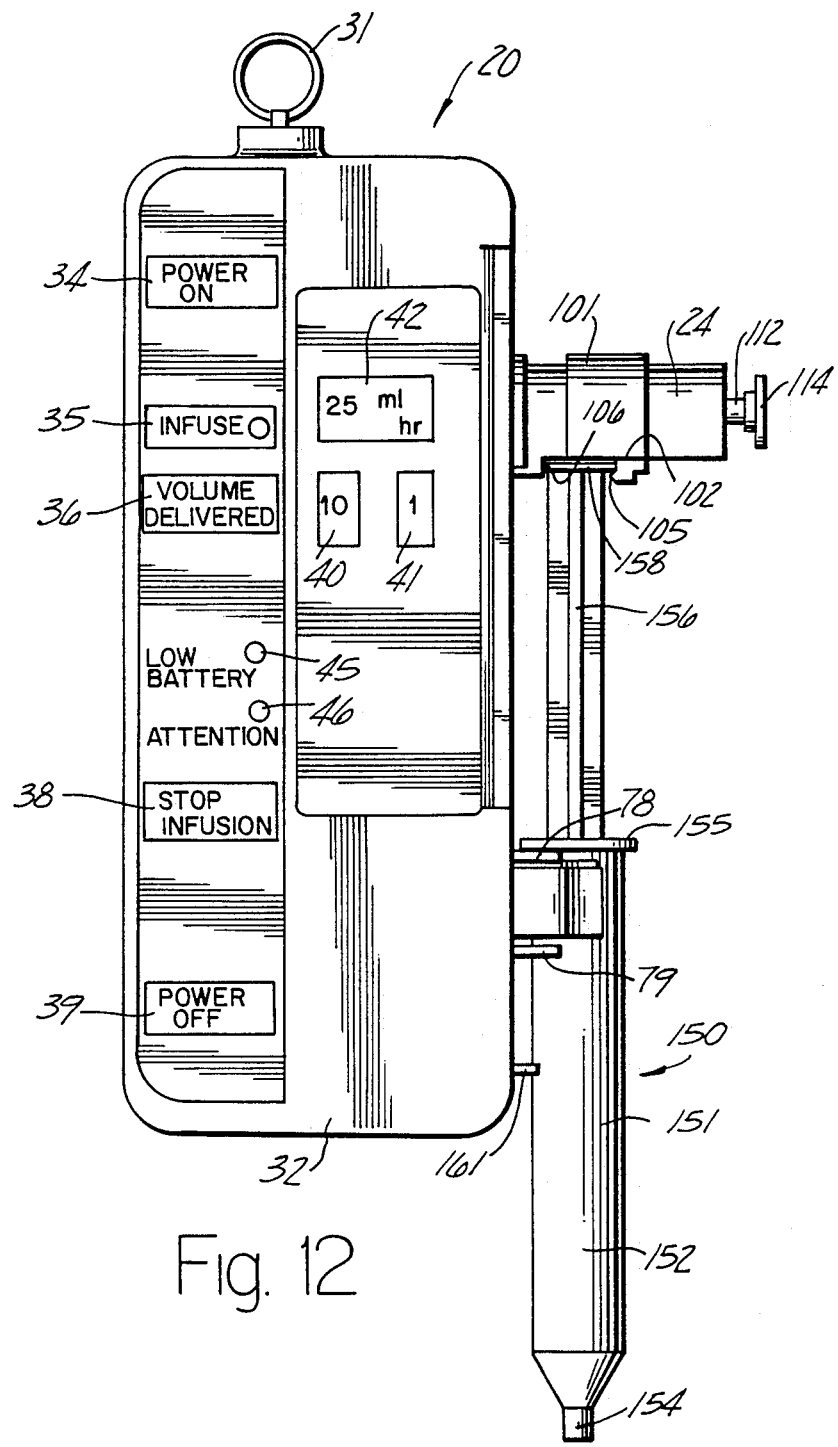
FIG. 12 is a plan view of the preferred embodiment of the syringe pump of the present invention illustrating a syringe mounted thereon as it appears in preparation for use.

General operation of syringe pump 20 will now be described in connection with FIGS. 11 and 12. A syringe 150 typically is prepared with liquid medication to be delivered to a patient at a prescribed delivery rate, such as in milliliters per hour. Syringe 150 is normally of the conventional type including a syringe barrel 151 having liquid medication 152 included therein. Distal tip 154 of the syringe barrel is provided for connection to a delivery line so that the liquid contents of the syringe may be passed therethrough and delivered to the patient. At the proximal end of barrel 151 there is usually a finger flange 155 on typical or conventional syringes. Extending out of the proximal end of syringe barrel 151 is a plunger 156 in the form of an elongate rod, the proximal end of which preferably terminates in a thumb disk 158 or the like.

Loaded syringe 150 is mounted onto syringe pump 20 in a few straightforward steps. The user first assures that driver mechanism clears thumb disk 158 of the syringe plunger by depressing button 114 inwardly thereby causing disengagement of the half nut from the lead screw within the interior of the housing. This disengagement allows the free movement of driver mechanism 24 to clear the plunger of the syringe Mounting of the syringe is then facilitated by the user grasping clamp 74 and pulling same outwardly so that the clamp slides linearly between clamp guides 78 and 79. Syringe barrel 151 is then positioned so that it rests against the protruding surfaces of cradle 160 and 161 formed on the outside surfaces of upper housing portion 28 and lower housing portion 29. Arm 75 of clamp 74 is then allowed to contact the outside surface of syringe barrel 151. As mentioned above, springs 82 and 84 inside the housing urge clamp 74 inwardly thereby holding the syringe barrel snugly and firmly in the cradle on the outside surface of the housing. At the same time, finger flange 155 at the proximal end of the syringe barrel is positioned so that it rests in contact directly on the outer surface of clamp guide 78. Accordingly, syringe barrel 151 of the syringe is now in a fixed and relatively immovable position during operation of the syringe pump.

Once the syringe barrel has been positioned as explained above, an automatic assessment and determination of its size takes place. Depending upon the size or diameter of syringe barrel 151, different contacts are made between electrical tab 89 on clamp 74 and one or more of the electrical strips on the printed circuit board, as set forth above. Thus, and for example only, if syringe 150 has a barrel of the conventional type of 20 cc capacity, electrical tab 89 may be in engagement with electrical strip 92. In that event, a circuit is established by virtue of these electrical contacts, informing the microprocessor circuitry that a 20 cc syringe is mounted on the housing. All delivery rates, timing intervals, the timing circuit, control circuit and calculations, may then be performed by virtue of the microprocessor and related circuitry in accordance with the specific size syringe automatically assessed to be in position for use in the syringe pump. No information need be provided by the user to the syringe pump with respect to the size of the syringe being used, since syringe size is automatically detected.

Driver mechanism 24 is brought into engagement with thumb disk 158 by a combination of straight-forward steps. Once again, button 114 may be depressed to release the internal engagement of the half nut and the lead screw so that the driver 24 may freely be slid to the position of the extending plunger rod of the syringe. Once button 114 is released, the internal engagement of the half nut and lead screw is once again established. Latch member 101 is then urged slightly outwardly by pulling on finger flanges 102. Thumb disk 158 of the syringe plunger is then slipped into engagement with abutment surface 106 on driver mechanism 24. Release of finger flanges 102 causes latch member 101 to move inwardly so that latch 105 is hooked over the protruding end of thumb disk 158 thereby capturing same in fixed position. The loaded syringe is now ready so that its contents may be delivered to the patient.

At this time, syringe pump 20 is typically hanging on a stand or the like in connection with ring 31. The user starts the procedure by first depressing POWER ON button 34 thereby activating the electrical circuitry of the syringe pump in accordance with the elements and features described above. If the battery power is low, light 45 will glow; if battery power is sufficient, light 45 remains off. If, for example, the liquid contents of syringe 150 are to be delivered at the rate of 25 milliliters per hour, the user pushes "tens" button 40 for two successive increments until the number "2' appears in the tens column of display 42. In similar fashion, the "ones" button 41 is depressed until it is incremented five times whereby the number "5" appears in the ones column of display 42. Once this rate of delivery has been established and also shown on display 42, the electrical circuitry of the syringe pump, having already assessed the size of the syringe mounted on the housing, functions through its microprocessor capabilities to deliver the contents of the syringe at the selected rate. The present invention is contemplated to be operative with conventional syringes of 5,10,20,30 and 60 cc capacity. It is understood that the present invention, however, is limited to neither these size syringes nor this number of different syringes.

Having selected the desired rate of delivery, the user depresses INFUSE button 35 signaling the initiation of DC motor 139 and subsequent movement of driver mechanism 24. This movement of the driver mechanism, in turn, causes plunger 156 to be pushed into syringe barrel 152 causing the liquid medication therein to be delivered through distal tip 154 into a medication line (not shown). Display 42 may be changed to show volume delivered from the commencement of operation by depression of VOLUME DELIVERED button 36. Display 42 will then read a number in milliliters, and may be programmed to display volume for a period of a few seconds after the VOLUME DELIVERED button has been depressed. If an occlusion occurs as a result of line blockage or the like, attention light 46 is lit and an audible alarm sounds, as described above. If, however, the occlusion detection circuit is activated as a result of end of cycle when medication delivery from the syringe barrel has been completed, the DC motor stops operation and attention light 46 comes on. The visual and audible signal corresponding to end of cycle, however, is different from the signal for line occlusion. At any time during operation of the syringe pump, the user may stop the operation of the syringe pump by depressing STOP INFUSION button 38. The unit is turned off by depressing POWER OFF button 39.

Thus, the present invention provides a syringe pump with a number of significant and notable improvements over presently known and available syringe pumps. Automatic sensing and determining of the size of the syringe mounted to the housing are provided, in which no wires are needed for connection to the electrical circuitry of the device. In addition, the front panel membrane buttons are also operative to energize or de-energize the selected functions without the need for wire connections between the front panel and the printed circuit board included within the housing. Elimination of guide rails for movement of the driver mechanism not only saves expense but considerable weight of the entire package. Further, the protective covering over the slot through which the driver mechanism moves is a significant safety feature for preventing the passage of foreign materials into the interior of the housing. Most significantly, the present syringe pump may be fabricated with relatively few components and inexpensive assembly, while providing the user with sophistication of operation and versatility of performance.

What is claimed is:

1. A syringe pump comprising:
   a housing having an elongate slot therethrough;
   a retainer mounted on said housing for receiving therein a syringe of the type including a barrel for holding liquid medication and a plunger movably positioned in the barrel for expelling the liquid medication therefrom;
   a driver movably mounted on said housing and being movable with respect to said slot, said driver positioned for engagement with said plunger for pushing said plunger into the barrel to thereby force the liquid medication out of the barrel;
   protection means attached to the driver, covering said slot and movable with respect to the slot to facilitate movement of the driver with respect to the slot and to move with the driver thereby providing constant protection of the slot so that foreign materials may be prevented from entering the housing through the slot;
   control means for regulating the movement of the driver against the plunger to thereby regulate delivery of the liquid medication from the barrel; and
   actuation means on the housing for permitting a user to select one or more functions under which the control means is to operate.

2. The pump of claim 1 wherein said protection means is a pair of flexible bands, one band attached to the driver and protectively extending over the slot in one direction, and the other band attached to the driver and protectively extending over the slot in the other direction.

3. A syringe pump comprising:
   a housing;
   a retainer mounted on said housing and movable relative thereto for receiving therein different size syringes each of the type including a barrel for holding liquid medication and a plunger movably positioned in the barrel for expelling the liquid medication therefrom, said retainer including first electrical contact means which are position-variable with respect to the housing depending upon the size of each syringe received in the retainer;
   a driver movably mounted on said housing for engagement with said plunger and for pushing said plunger into the barrel to thereby force the liquid medication out of the barrel;
   control means within said housing for regulating the movement of the driver against the plunger to thereby regulate delivery of the liquid medication from the barrel;
   second electrical contact means within said housing positioned to be contacted by the first electrical contact means of said retainer for producing an electrical signal representative of the size of the syringe received in the retainer, said signal being receivable by the control means so that movement of the driver is related to the size of the syringe received in the retainer; and
   actuation means on the housing for permitting a user to select one or more functions under which the control means is to operate.

4. The pump of claim 3 wherein said first electrical contact means includes a plurality of tabs and said second electrical contact means includes a plurality of strips arranged so that one or more different strips are contacted by the tabs for different sizes of syringes received in the retainer.

5. The pump of claim 4 wherein the control means includes memory storage means for identifying the electrical signal received from said electrical contact means as representative of a syringe of one of a series of sizes pre-programmed into said storage means.

6. The pump of claim 4 wherein said control means includes a printed circuit board positioned within said housing, wherein said electrical strips are included on said circuit board.

7. The pump of claim 4 wherein the retainer includes a manually operative clamp of such size and shape to grasp different diameter barrels of the syringe.

8. The pump of claim 7 wherein said clamp has said tabs mounted thereon, said clamp being slidably mounted on said housing for linear movement with respect thereto, said tabs being so arranged to contact one or more different electrical strips on said printed circuit board depending upon the linear position of said clamp which is changeable according to the size syringe barrel held by said clamp.

9. A syringe pump comprising:
   a housing having a raised elongate bearing surface on an outside portion thereof;
   a retainer mounted on said housing for receiving therein a syringe of the type including a barrel for holding liquid medication and a plunger movably positioned in the barrel for expelling the liquid medication therefrom, said retainer including first electrical contact means which are position-variable with respect to the housing depending upon the size of the syringe received in the retainer;
   a driver movably mounted on said housing and in sliding contact with said raised bearing surface, said driver positioned for engagement with said plunger and said raised bearing surface for pushing said plunger into the barrel to thereby force the liquid medication out of the barrel;
   control means within said housing for regulating the movement of the driver against the plunger to thereby regulate delivery of the liquid medication from the barrel;
   second electrical contact means within said housing positioned to be contacted by the first electrical contact means of said retainer for producing an electrical signal representative of the size of the syringe received in the retainer, said signal being receivable by the control means so that movement of the driver is related to the size of the syringe received in the retainer; and depressible actuation means mounted on said housing for manual access by a user and associated with said control means to permit the user to select one or more functions under which said control means is to operate, said actuation means including an electrically conductive material positioned to contact an actuation element associated with said control means when the actuation means is depressed by the user to electrically energize or de-energize the control means for operation of the selected function.

* * * * *